US005231011A

United States Patent [19]

Hillyard et al.

[11] Patent Number: 5,231,011

[45] Date of Patent: Jul. 27, 1993

[54] SEGREGATED FOLDING DETERMINANTS FOR SMALL DISULFIDE-RICH PEPTIDES

[75] Inventors: David R. Hillyard, Holliday; Baldomero M. Olivera, Salt Lake City, both of Utah

[73] Assignee: University of Utah, Salt Lake City, Utah

[21] Appl. No.: 689,693

[22] Filed: Apr. 18, 1991

[51] Int. Cl.[5] ........................ C12P 21/06; C12P 21/00; C07K 7/00; C07K 15/00

[52] U.S. Cl. .................................. 435/69.7; 435/68.1; 435/69.1; 435/172.3; 530/333; 530/300; 530/334; 530/338; 530/857; 530/350

[58] Field of Search ............... 530/333, 350, 300, 334, 530/338, 857; 435/68.1, 69.7, 69.1, 172.3

[56] References Cited

PUBLICATIONS

Olivera et al. (1990) *Science*, vol. 249, Jul. 1990, pp. 257-263.

Olivera et al. (1987), *Biochemistry*, vol. 26, No. 8, 1987, pp. 2086-2090.

Woodward et al., *Eubo Journal*, vol. 9, No. 4, pp. 1015-1020, 1990.

Becker et al., *Eur. J. Biochem*, vol. 185, 1989, pp. 79-84.

Hillyard et al., *Biochemistry*, vol. 28, No. 1, 1989, pp. 358-361.

Cruz et al., *Biochemistry*, vol. 28, No. 8, 1989, pp. 3437-3442.

*Primary Examiner*—Robert A. Wax

*Assistant Examiner*—Keith D. Hendricks

*Attorney, Agent, or Firm*—Thorpe, North & Western

[57] ABSTRACT

The preparation of small peptides with multiple disulfide bonds is accomplished by forming a prepropeptide with an N-terminal excised region separated from the cysteine-rich peptide by one or more cleavable amino acid residues. The excised region preferably consists of an N-terminal end providing a hydrophobic signal sequence domain having up to approximately 25 amino acids, and an intermediate central propeptide domain having a variable length of between about 5-50 amino acids. The N-terminal excised region serves as a folding template to direct the formation of specific disulfide bonds in the cysteine-rich peptide. The cysteine-rich peptide is cleaved by enzymes releasing the biologically active peptide.

13 Claims, No Drawings

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 71 amino acids
( B ) TYPE: amino acid
( D ) TOPOLOGY: linear ( i i ) MOLECULE TYPE: peptide ( i x ) FEATURE:

( A ) NAME/KEY: Prepropeptide sequence for four-loop MVIIB Omega conotoxin from Conus magus.
( C ) IDENTIFICATION METHOD: Libraries were created using oligo-dT primed pUC13 vector ( x i ) SEQUENCE DESCRIPTION: SEQ ID NO:1:

```
Met Lys Leu Thr Cys Val Val Ile Val Ala Val Leu Leu Leu Thr Ala
-45                 -40                 -35                 -30

Cys Gln Leu Ile Thr Ala Asp Asp Ser Arg Gly Thr Gln Lys His Arg
                -25                 -20                 -15

Ala Leu Arg Ser Asp Thr Lys Leu Ser Met Ser Thr Arg Cys Lys Gly
            -10                 -5                  1

Lys Gly Ala Ser Cys His Arg Thr Ser Tyr Asp Cys Cys Thr Gly Ser
    5                   10                  15

Cys Asn Arg Gly Lys Cys Gly
20                  25
```

( 2 ) INFORMATION FOR SEQ ID NO:2:

( i ) SEQUENCE CHARACTERISTICS:
( A ) LENGTH: 25 amino acids
( B ) TYPE: amino acids
( D ) TOPOLOGY: linear ( i i ) MOLECULE TYPE: peptide ( i x ) FEATURE:
( A ) NAME/KEY: MVIIB Omega conotoxin.
( C ) IDENTIFICATION METHOD: Direct peptide sequencing of purified Conus magus venom ( x i ) SEQUENCE DESCRIPTION: SEQ ID NO:2:

```
Cys Lys Gly Lys Gly Ala Ser Cys His Arg Thr Ser Tyr Asp Cys Cys
                5                   10                  15

Thr Gly Ser Cys Asn Arg Gly Lys Cys
            20                  25
```

( 2 ) INFORMATION FOR SEQ ID NO:3:

( i ) SEQUENCE CHARACTERISTICS:
( A ) LENGTH: 73 amino acids

-continued ( B ) TYPE: amino acid
( D ) TOPOLOGY: linear ( i i ) MOLECULE TYPE: peptide ( i x ) FEATURE:
( A ) NAME/KEY: Prepropeptide sequence for four-loop GVIA Omega conotoxin from Conus geographus.
( C ) IDENTIFICATION METHOD: Libraries were created using oligo- dT primed pUC13 vector ( x i ) SEQUENCE DESCRIPTION: SEQ ID NO:3:

```
Met Lys Leu Thr Cys Val Val Ile Val Ala Val Leu Leu Leu Thr Ala
-45                 -40                 -35                 -30

Cys Gln Leu Ile Thr Ala Asp Asp Ser Arg Gly Thr Gln Lys His Arg
                -25                 -20                 -15

Ala Leu Gly Ser Thr Thr Glu Leu Ser Leu Ser Thr Arg Cys Lys Ser
            -10                 -5                   1

Pro Gly Ser Ser Cys Ser Pro Thr Ser Tyr Asn Cys Cys Arg Ser Cys
     5                  10                  15

Asn Pro Tyr Thr Lys Arg Cys Tyr Gly
 20                  25
```

( 2 ) INFORMATION FOR SEQ ID NO:4:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( i x ) FEATURE:
( A ) NAME/KEY: GVIA Omega conotoxin.
( C ) IDENTIFICATION METHOD: Direct peptide sequencing of purified Conus geographus venom ( x i ) SEQUENCE DESCRIPTION: SEQ ID NO:4:

```
Cys Lys Ser Pro Gly Ser Ser Cys Ser Pro Thr Ser Tyr Asn Cys Cys
 1               5                  10                  15

Arg Ser Cys Asn Pro Tyr Thr Lys Arg Cys Tyr
             20                  25
```

( 2 ) INFORMATION FOR SEQ ID NO:5:

( i ) SEQUENCE CHARACTERISTICS:
( A ) LENGTH: 78 amino acids
( B ) TYPE: amino acid
( D ) TOPOLOGY: linear ( i i ) MOLECULE TYPE: peptide ( i x ) FEATURE:
( A ) NAME/KEY: Prepropeptide sequence for four loop King Kong (kk0) conotoxin from Conus textile.
( C ) IDENTIFICATION METHOD: Library was constructed using polyA selected mRNA transcripts purified from Conus textile venom duct tissue and cloned into the Okyama-Berg oligo-dT primed plasmid pSV7186.

( x i ) SEQUENCE DESCRIPTION: SEQ ID NO:5:

```
Met Lys Leu Thr Cys Met Met Ile Val Ala Val Leu Phe Leu Thr Ala
    -50                 -45                 -40

Trp Thr Phe Ala Thr Ala Asp Asp Pro Arg Asn Gly Leu Gly Asn Ser
-35                 -30                 -25                 -20

Phe Ser Asn Ala His His Glu Met Lys Asn Pro Glu Ala Ser Lys Leu
                -15                 -10                 -5
```

-continued

Asn Lys Arg Trp Cys Lys Gln Ser Gly Glu Met Cys Asn Leu Leu Asp
1 5 10

Gln Asn Cys Cys Asp Gly Tyr Cys Ile Val Leu Val Cys Thr
15 20 25

( 2 ) INFORMATION FOR SEQ ID NO:6:

( i ) SEQUENCE CHARACTERISTICS:
( A ) LENGTH: 27 amino acids
( B ) TYPE: amino acid
( D ) TOPOLOGY: linear ( i i ) MOLECULE TYPE: peptide ( i x ) FEATURE:
( A ) NAME/KEY: King Kong (kk0) conotoxin
( C ) IDENTIFICATION METHOD: Direct peptide sequencing of purified Conus textile venom ( x i ) SEQUENCE DESCRIPTION: SEQ ID NO:6:

Trp Cys Lys Gln Ser Gly Glu Met Cys Asn Leu Leu Asp Gln Asn Cys
1 5 10 15

Cys Asp Gly Tyr Cys Ile Val Leu Val Cys Thr
20 25

( 2 ) INFORMATION FOR SEQ ID NO:7:

( i ) SEQUENCE CHARACTERISTICS:
( A ) LENGTH: 77 amino acids
( B ) TYPE: amino acid
( D ) TOPOLOGY: linear ( i i ) MOLECULE TYPE: peptide ( i x ) FEATURE:
( A ) NAME/KEY: Prepropeptide sequence for four loop King Kong (kk1) conotoxin from Conus textile.
( C ) IDENTIFICATION METHOD: Library was constructed using polyA selected mRNA transcripts purified from Conus textile venom duct tissue and cloned into the Okyama-Berg oligo-dT primed plasmid pSV7186.

( x i ) SEQUENCE DESCRIPTION: SEQ ID NO:7:

Met Lys Leu Thr Cys Met Met Ile Val Ala Val Leu Phe Leu Thr Ala
-50 -45 -40

Trp Thr Phe Ala Thr Ala Asp Asp Ser Gly Asn Gly Leu Glu Asn Ser
-35 -30 -25 -20

Phe Ser Lys Ala His His Glu Met Lys Asn Pro Glu Ala Ser Lys Leu
-15 -10 -5

Asn Lys Arg Cys Ile Glu Gln Phe Asp Pro Cys Glu Met Ile Arg His
1 5 10

Thr Cys Cys Val Gly Val Cys Phe Leu Met Ala Cys Ile
15 20 25

( 2 ) INFORMATION FOR SEQ ID NO:8:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( i x ) FEATURE:
( A ) NAME/KEY: King Kong (kk1) conotoxin.
( B ) IDENTIFICATION METHOD: Direct peptide sequencing of purified Conus textile venom ( x i ) SEQUENCE DESCRIPTION: SEQ ID NO:8:

-continued

| | | | | | | | | | | | | | | | |
|---|---|---|---|---|---|---|---|---|---|---|---|---|---|---|---|
| Cys | Ile | Glu | Gln | Phe | Asp | Pro | Cys | Glu | Met | Ile | Arg | His | Thr | Cys | Cys |
| 1 | | | | 5 | | | | | 10 | | | | | 15 | |
| Val | Gly | Val | Cys | Phe | Leu | Met | Ala | Cys | Ile | | | | | | |
| | | | 20 | | | | | 25 | | | | | | | |

( 2 ) INFORMATION FOR SEQ ID NO:9:

( i ) SEQUENCE CHARACTERISTICS:
( A ) LENGTH: 77 amino acids
( B ) TYPE: amino acid
( D ) TOPOLOGY: linear ( i i ) MOLECULE TYPE: peptide ( i x ) FEATURE:
( A ) NAME/KEY: Prepropeptide sequence for four loop King Kong (kk2) conotoxin from Conus textile.
( C ) IDENTIFICATION METHOD: Library was constructed using polyA selected mRNA transcripts purified from Conus textile venom duct tissue and cloned into the Okyama-Berg oligo-dT primed plasmid pSV7186.

( x i ) SEQUENCE DESCRIPTION: SEQ ID NO:9:

| | | | | | | | | | | | | | | | |
|---|---|---|---|---|---|---|---|---|---|---|---|---|---|---|---|
| Met | Lys | Leu | Thr | Cys | Met | Met | Ile | Val | Ala | Val | Leu | Phe | Leu | Thr | Ala |
| | -50 | | | | | -45 | | | | | -40 | | | | |
| Trp | Thr | Phe | Val | Thr | Ala | Asp | Asp | Ser | Gly | Asn | Gly | Leu | Glu | Asn | Ser |
| -35 | | | | | -30 | | | | | -25 | | | | | -20 |
| Phe | Ser | Lys | Ala | His | His | Glu | Met | Lys | Asn | Pro | Glu | Ala | Ser | Asn | Leu |
| | | | | -15 | | | | | -10 | | | | | -5 | |
| Asn | Lys | Arg | Cys | Ala | Pro | Phe | Leu | His | Pro | Cys | Thr | Phe | Phe | Phe | Pro |
| | | | 1 | | | | 5 | | | | | 10 | | | |
| Thr | Cys | Cys | Asn | Ser | Tyr | Cys | Val | Gln | Phe | Ile | Cys | Leu | | | |
| | 15 | | | | | 20 | | | | | 25 | | | | |

( 2 ) INFORMATION FOR SEQ ID NO:10:

( i ) SEQUENCE CHARACTERISTICS:
( A ) LENGTH: 26 amino acids
( B ) TYPE: amino acid
( D ) TOPOLOGY: linear ( i i ) MOLECULE TYPE: peptide ( i x ) FEATURE:
( A ) NAME/KEY: King Kong (kk2) conotoxin.
( C ) IDENTIFICATION METHOD: Direct peptide sequencing of purified Conus textile venom ( x i ) SEQUENCE DESCRIPTION: SEQ ID NO:10:

| | | | | | | | | | | | | | | | |
|---|---|---|---|---|---|---|---|---|---|---|---|---|---|---|---|
| Cys | Ala | Pro | Phe | Leu | His | Pro | Cys | Thr | Phe | Phe | Phe | Pro | Thr | Cys | Cys |
| 1 | | | | 5 | | | | | 10 | | | | | 15 | |
| Asn | Ser | Tyr | Cys | Val | Gln | Phe | Ile | Cys | Leu | | | | | | |
| | | | 20 | | | | | 25 | | | | | | | |

( 2 ) INFORMATION FOR SEQ ID NO:11:

( i ) SEQUENCE CHARACTERISTICS:
( A ) LENGTH: 68 amino acids
( B ) TYPE: amino acid
( D ) TOPOLOGY: linear ( i i ) MOLECULE TYPE: peptide ( i x ) FEATURE:
( A ) NAME/KEY: Prepropeptide sequence for three loop conotoxin from Circler conotoxin from Conus textile
( C ) IDENTIFICATION METHOD: Libraries were created using oligo- dT primed pUC13 vector -continued ( x i ) SEQUENCE DESCRIPTION: SEQ ID NO:11:

Met Ser Lys Leu Gly Ala Leu Leu Thr Ile Cys Leu Leu Leu Phe Ser
-50 -45 -40

Leu Thr Ala Val Pro Leu Asp Gly Asp Gln His Ala Asp Gln Pro Ala
-35 -30 -25

Gln Arg Leu Gln Asp Arg Ile Pro Thr Glu Asp His Pro Leu Phe Asp
-20 -15 -10 -5

Pro Asn Lys Arg Cys Cys Pro Pro Val Ala Cys Asn Met Gly Cys Lys
1 5 10

Pro Cys Cys Gly
15

( 2 ) INFORMATION FOR SEQ ID NO:12:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i x ) FEATURE:
( A ) NAME/KEY: Circler conotoxin.
( C ) IDENTIFICATION METHOD: Direct peptide sequencing of purified Conus textile venom ( x i ) SEQUENCE DESCRIPTION: SEQ ID NO:12:

Cys Cys Pro Pro Val Ala Cys Asn Met Gly Cys Lys Pro Cys Cys
1 5 10 15

( 2 ) INFORMATION FOR SEQ ID NO:13:

( i ) SEQUENCE CHARACTERISTICS:
( A ) LENGTH: 64 amino acids
( B ) TYPE: amino acid
( D ) TOPOLOGY: linear ( i i ) MOLECULE TYPE: peptide ( i x ) FEATURE:
( A ) NAME/KEY: Prepropeptide sequence for two loop GI conooxin from Conus geographus.
( C ) IDENTIFICATION METHOD: Libraries were created using oligo- dT primed pUC13 vector ( x i ) SEQUENCE DESCRIPTION: SEQ ID NO:13:

Met Gly Met Arg Met Met Phe Thr Val Phe Leu Leu Val Val Leu Ala
-45 -40 -35

Thr Thr Val Val Ser Phe Pro Ser Glu Arg Ala Ser Asp Gly Arg Asp
-30 -25 -20

Asp Thr Ala Lys Asp Glu Gly Ser Asp Met Asp Lys Leu Val Glu Lys
-15 -10 -5

Lys Glu Cys Cys Asn Pro Ala Cys Gly Arg His Tyr Ser Cys Gly Arg
1 5 10 15

( 2 ) INFORMATION FOR SEQ ID NO:14:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( i x ) FEATURE:
( A ) NAME/KEY: GI Conotoxin
( C ) IDENTIFICATION METHOD: Direct peptide sequencing of purified Conus geographus venom ( x i ) SEQUENCE DESCRIPTION: SEQ ID NO:14:

Glu Cys Cys Asn Pro Ala Cys Gly Arg His Tyr Ser Cys
5 10

( 2 ) INFORMATION FOR SEQ ID NO:15:

( i ) SEQUENCE CHARACTERISTICS:
( A ) LENGTH: 20 base pairs
( B ) TYPE: nucleic
( C ) STRANDEDNESS: single
( D ) TOPOLOGY: linear ( i x ) FEATURE:
( D ) OTHER INFORMATION: In sequence R =A or G and
Y =T or C ( x i ) SEQUENCE DESCRIPTION: SEQ ID NO:15:

CCRTCRCARCARTTYTGRTC 20

( 2 ) INFORMATION FOR SEQ ID NO:16:

( i ) SEQUENCE CHARACTERISTICS:
( A ) LENGTH: 14 base pairs
( B ) TYPE: nucleic
( C ) STRANDEDNESS: single
( D ) TOPOLOGY: linear ( i x ) FEATURE:
( D ) OTHER INFORMATION: In sequence R =A or G.
Y =T or C and N =ATG or C ( x i ) SEQUENCE DESCRIPTION: SEQ ID NO:16:

TTRCACATYTCNCC 14

( 2 ) INFORMATION FOR SEQ ID NO:17:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( i x ) FEATURE:
( A ) NAME/KEY: amino acid sequence from King Kong KKO
conotoxin
( B ) IDENTIFICATION METHOD: sequencer ( x i ) SEQUENCE DESCRIPTION: SEQ ID NO:17:

Asp Gln Asn Cys Cys Asp Gly
5

( 2 ) INFORMATION FOR SEQ ID NO:18:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( i x ) FEATURE:
( A ) NAME/KEY: amino acid sequence from King Kong KKO
conotoxin
( B ) IDENTIFICATION METHOD: sequencer ( x i ) SEQUENCE DESCRIPTION: SEQ ID NO:18:

Gly Glu Met Cys Asn
5

( 2 ) INFORMATION FOR SEQ ID NO:19:

-continued ( i ) SEQUENCE CHARACTERISTICS:
( A ) LENGTH: 45 amino acids
( B ) TYPE: amino acid
( D ) TOPOLOGY: linear ( i i ) MOLECULE TYPE: peptide ( i x ) FEATURE:
( A ) NAME/KEY: Signal/Pro sequence for synthesis of four-loop MVIIB Omega conotoxin
( C ) IDENTIFICATION METHOD: Libraries were created using oligo- dT primed pUC13 vector ( x i ) SEQUENCE DESCRIPTION: SEQ ID NO:19:

Met Lys Leu Thr Cys Val Val Ile Val Ala Val Leu Leu Leu Thr Ala
1 5 10 15

Cys Gln Leu Ile Thr Ala Asp Asp Ser Arg Gly Thr Gln Lys His Arg
20 25 30

Ala Leu Arg Ser Asp Thr Lys Leu Ser Met Ser Thr Arg
35 40 45

( 2 ) INFORMATION FOR SEQ ID NO:20:

( i ) SEQUENCE CHARACTERISTICS:
( A ) LENGTH: 45 amino acids
( B ) TYPE: amino acid
( D ) TOPOLOGY: linear ( i i ) MOLECULE TYPE: peptide ( i x ) FEATURE:
( A ) NAME/KEY: Signal/Pro sequence for synthesis of four-loop GVIA Omega conotoxin
( C ) IDENTIFICATION METHOD: Libraries were created using oligo- dT primed pUC13 vector ( x i ) SEQUENCE DESCRIPTION: SEQ ID NO:20:

Met Lys Leu Thr Cys Val Val Ile Val Ala Val Leu Leu Leu Thr Ala
1 5 10 15

Cys Gln Leu Ile Thr Ala Asp Asp Ser Arg Gly Thr Gln Lys His Arg
20 25 30

Ala Leu Gly Ser Thr Thr Glu Leu Ser Leu Ser Thr Arg
35 40 45

( 2 ) INFORMATION FOR SEQ ID NO:21:

( i ) SEQUENCE CHARACTERISTICS:
( A ) LENGTH: 51 amino acids
( B ) TYPE: amino acid
( D ) TOPOLOGY: linear ( i i ) MOLECULE TYPE: peptide ( i x ) FEATURE:
( A ) NAME/KEY: Signal/Pro sequence for synthesis of four loop King Kong (kk0) conotoxin
( C ) IDENTIFICATION METHOD: Library was constructed using polyA selected mRNA transcripts purified from Conus textile venom duct tissue and cloned into the Okyama-Berg oligo-dT primed plasmid pSV7186.

( x i ) SEQUENCE DESCRIPTION: SEQ ID NO:21:

Met Lys Leu Thr Cys Met Met Ile Val Ala Val Leu Phe Leu Thr Ala
1 5 10 15

Trp Thr Phe Ala Thr Ala Asp Asp Pro Arg Asn Gly Leu Gly Asn Ser
20 25 30

Phe Ser Asn Ala His His Glu Met Lys Asn Pro Glu Ala Ser Lys Leu
35 40 45

Asn Lys Arg

-continued

50

(2) INFORMATION FOR SEQ ID NO:22:

(i) SEQUENCE CHARACTERISTICS:
(A) LENGTH: 51 amino acids
(B) TYPE: amino acid
(D) TOPOLOGY: linear (ii) MOLECULE TYPE: peptide (ix) FEATURE:
(A) NAME/KEY: Signal/Pro sequence for synthesis of four loop King Kong (kk1) conotoxin
(C) IDENTIFICATION METHOD: Library was constructed using polyA selected mRNA transcripts purified from Conus textile venom duct tissue and cloned into the Okyama-Berg oligo-dT primed plasmid pSV7186.

(xi) SEQUENCE DESCRIPTION: SEQ ID NO:22:

```
Met Lys Leu Thr Cys Met Met Ile Val Ala Val Leu Phe Leu Thr Ala
 1               5                  10                  15

Trp Thr Phe Ala Thr Ala Asp Asp Ser Gly Asn Gly Leu Glu Asn Ser
            20                  25                  30

Phe Ser Lys Ala His His Glu Met Lys Asn Pro Glu Ala Ser Lys Leu
        35                  40                  45

Asn Lys Arg
    50
```

(2) INFORMATION FOR SEQ ID NO:23:

(i) SEQUENCE CHARACTERISTICS:
(A) LENGTH: 51 amino acids
(B) TYPE: amino acid
(D) TOPOLOGY: linear (ii) MOLECULE TYPE: peptide (ix) FEATURE:
(A) NAME/KEY: Signal/Pro sequence for synthesis of four loop King Kong (kk2) conotoxin
(C) IDENTIFICATION METHOD: Library was constructed using polyA selected mRNA transcripts purified from Conus textile venom duct tissue and cloned into the Okyama-Berg oligo-dT primed plasmid pSV7186.

(xi) SEQUENCE DESCRIPTION: SEQ ID NO:23:

```
Met Lys Leu Thr Cys Met Met Ile Val Ala Val Leu Phe Leu Thr Ala
 1               5                  10                  15

Trp Thr Phe Val Thr Ala Asp Asp Ser Gly Asn Gly Leu Glu Asn Ser
            20                  25                  30

Phe Ser Lys Ala His His Glu Met Lys Asn Pro Glu Ala Ser Asn Leu
        35                  40                  45

Asn Lys Arg
    50
```

(2) INFORMATION FOR SEQ ID NO:24:

(i) SEQUENCE CHARACTERISTICS:
(A) LENGTH: 52 amino acids
(B) TYPE: amino acid
(D) TOPOLOGY: linear (ii) MOLECULE TYPE: peptide (ix) FEATURE:
(A) NAME/KEY: Signal/Pro sequence for synthesis of three loop conotoxin from Circler conotoxin
(C) IDENTIFICATION METHOD: Libraries were created -continued using oligo- dT primed pUC13 vector ( x i ) SEQUENCE DESCRIPTION: SEQ ID NO:24:

| | | | | | | | | | | | | | | | |
|---|---|---|---|---|---|---|---|---|---|---|---|---|---|---|---|
| Met | Ser | Lys | Leu | Gly | Ala | Leu | Leu | Thr | Ile | Cys | Leu | Leu | Leu | Phe | Ser |
| 1 | | | | 5 | | | | | 10 | | | | | 15 | |
| Leu | Thr | Ala | Val | Pro | Leu | Asp | Gly | Asp | Gln | His | Ala | Asp | Gln | Pro | Ala |
| | | | 20 | | | | | 25 | | | | | 30 | | |
| Gln | Arg | Leu | Gln | Asp | Arg | Ile | Pro | Thr | Glu | Asp | His | Pro | Leu | Phe | Asp |
| | | 35 | | | | | 40 | | | | | 45 | | | |
| Pro | Asn | Lys | Arg | | | | | | | | | | | | |
| | 50 | | | | | | | | | | | | | | |

( 2 ) INFORMATION FOR SEQ ID NO:25:

( i ) SEQUENCE CHARACTERISTICS:
( A ) LENGTH: 49 amino acids
( B ) TYPE: amino acid
( D ) TOPOLOGY: linear ( i i ) MOLECULE TYPE: peptide ( i x ) FEATURE:
( A ) NAME/KEY: Signal/Pro sequence for synthesis of two loop GI conooxin
( C ) IDENTIFICATION METHOD: Libraries were created using oligo- dT primed pUC13 vector ( x i ) SEQUENCE DESCRIPTION: SEQ ID NO:25:

| | | | | | | | | | | | | | | | |
|---|---|---|---|---|---|---|---|---|---|---|---|---|---|---|---|
| Met | Gly | Met | Arg | Met | Met | Phe | Thr | Val | Phe | Leu | Leu | Val | Val | Leu | Ala |
| 1 | | | | 5 | | | | | 10 | | | | | 15 | |
| Thr | Thr | Val | Val | Ser | Phe | Pro | Ser | Glu | Arg | Ala | Ser | Asp | Gly | Arg | Asp |
| | | | 20 | | | | | 25 | | | | | 30 | | |
| Asp | Thr | Ala | Lys | Asp | Glu | Gly | Ser | Asp | Met | Asp | Lys | Leu | Val | Glu | Lys |
| | | 35 | | | | | 40 | | | | | 55 | | | |
| Lys | | | | | | | | | | | | | | | |

SEGREGATED FOLDING DETERMINANTS FOR SMALL DISULFIDE-RICH PEPTIDES

This invention was made with government support under Contract No. N00014-88-K-0178 awarded by the Department of the Navy and under Contract No. GM-22737 awarded by the Department of Health and Human Services. The government has certain rights in the invention.

BACKGROUND OF THE INVENTION

This invention relates to a method for forming biologically active peptides with specific disulfide linkages. This invention also relates to the synthesis of prepropeptides containing an N-terminal template region which, when combined with a mature peptide region containing multiple cysteine residues, results in specific disulfide bonds being formed in the mature peptide region.

The obtaining of small biologically active cysteine-rich disulfide containing peptides, i.e. those containing 10 to 30, or even more, amino acids, which have the same folding pattern presents a problem in synthesis. The obtaining of such peptides is highly desirable for designing drug delivery systems which are targeted to specific protein receptors, or which interfere with the function of these receptor targets. These peptides have applications in biotechnology, particularly for the pharmaceutical industry and in agriculture. However, when such small peptides, such as found in nature in the venom of the Conus snail, are synthesized by conventional synthetic methods, the formation of the disulfide bonds is non-specific and, when oxidized, the peptides appear to fold in many different disulfide configurations rather than in a specific biologically active form found in the naturally occurring peptides.

The conotoxins are a set of small peptide ligands found in the venom of predatory cone snails. These peptides, used by the cone snails to capture their prey, bind and interfere with the function of a diverse set of receptors and ion channel targets. Compared with most polypeptide toxins, the cone snails use much smaller molecules (typically 10–30 amino acids) wherein the biologically active conformation is shaped by the formation of disulfide bonds between specific cysteine residues Conotoxin peptides have some of the highest known densities of disulfide bonding in any biological system. Peptides from Conus venoms have been isolated that are only 12 amino acids long with three disulfide bonds.

Despite their relatively small size, these peptide ligands can bind with remarkably high affinities to the receptor targets in the prey. ω-Conotoxins have subpicomolar $K_D$s for certain neuronal Ca channel targets. In general, only one disulfide bonded configuration (i.e. the conformation found in the natural peptide) exhibits high affinity for the specific receptor target.

Although some conotoxins have only two disulfide bonds (notably the α-conotoxins which target to nicotinic acetylcholine receptors), more commonly the major paralytic conotoxins found in Conus venom have three disulfide bonds (in the fish-hunting cones, the μ-conotoxins which target to muscle voltage-sensitive Na channels and the ω-conotoxins which target to presynaptic voltage sensitive Ca channels). For the latter, there are 15 possible disulfide bonded configurations. Folding smaller peptides into one specific configuration is a biochemical problem which the cone snails had to solve before they could efficiently use such small peptides as high affinity ligands for paralysing their prey. When the peptides are chemically synthesized and cysteine residues oxidized after synthesis, they often appear to fold in a variety of different disulfide configurations, which are different from the biologically active form found in the venom. In the chemical synthesis of μ-conotoxin, even after optimizing for the increased yield, the overall yield of the correctly disulfide bonded configuration was still $<10\%$.

Small, conformationally constrained peptides are ideal for a wide variety of biotechnology applications. Their small size facilitates access to specific target receptors. Specific cross-linking of disulfide bonds allows these small peptides to assume a relatively rigid structure that increases the probability of high affinity interaction with target molecules. Still, the variation of peptide structure afforded by variation in amino acid sequence in such peptides is enormous. Natural variants among peptides following this architectural design have been found to target a great diversity of target types. Molecules of this type have an expanding usefulness as agents capable of targeting a vast variety of receptors and ion channels on the surface of many different cell types. These molecules are useful in the design and testing of drugs targeting to variety of therapeutically important components, and in the design of agriculturally important agents. In addition, they have a more general potential as ligands used for interaction with broad classes of proteins and other biologically relevant macromolecules.

If these small peptides containing multiple disulfide bonds are synthesized by conventional synthetic methods, the formation of the disulfide bonds is non-specific. In nature this problem is solved by the formation of prepropeptides that fold in a conformation that allows the cysteine residues of the toxin portion of the peptide chain to form the disulfide bonds in the positions necessary for activity. It would be desirable to provide an atmosphere where the portions of the prepropeptides that contain the folding instructions could be synthesized and attached to either the natural or synthetic small peptides that contain multiple cysteine residues. Such synthesis would desirably be performed by cloning techniques or by conventional means such as solution phase synthesis, solid phase synthesis or a combination of these two techniques. Thus, the final prepropeptide resulting from such combination would have the disulfide bonds in the proper position for activity. Once synthesized, the pre- and pro- portions of the molecule could be cleaved without disturbing the disulfide bonds, thereby releasing a cystiene-rich bioactive peptide.

OBJECTS AND SUMMARY OF THE INVENTION

It is an object of the present invention to provide a class of N-terminal polypeptides which function as template region in the synthesis of prepropeptides for the formation at the C-terminal end of cysteine-rich peptides having specific disulfide linkages and configuration.

It is also an object of this invention to provide a method for forming biological active peptides with specific disulfide linkages through the formation of prepropeptides wherein the C-terminal end of the prepropeptide consists of the desired bioactive peptide and the remainder through the N-terminal end, referred to as the excised end, contains a region having folding template activity, both in vivo and in vitro, for directing the formation of specific disulfide bonds in the bioactive cysteine-rich peptide at the C-terminal end.

It is also an object of this invention to provide a method for the preparation of relatively small cysteine-rich peptides having specific disulfide bond configurations prepared by directing specific disulfide bond formation using a region of the excised end of the prepropeptide as a folding template.

These and other objects may be accomplished by formation of a class of prepropeptide molecules having a general architectural theme consisting of a C-terminal cysteine-rich mature peptide region and an excised region preferably having two domains, the first being the N-terminal end which consists of a hydrophobic signal sequence domain and a central propeptide domain as more specifically defined in the following formula wherein the excised region serves as a folding template to direct the formation of specific disulfide bonds in the mature peptide region. Between the mature peptide region and the excised region there is locate a cleavage site for the excision of the mature cysteine-rich peptide from the prepropeptide molecule.

The prepropeptide is made up of an N-terminal template peptide preferably consisting of an N-terminal end providing a hydrophobic signal sequence domain and an intermediate central propeptide domain having a variable length and a C-terminal end providing a cleavage site attached to the active region containing the multiple disulfide bonds from which said mature peptide can be enzymatically cleaved. Although described as having two domains, the N-terminal peptide may have only the hydrophobic signal or propeptide domain as long as that domain or region serves as a folding template to direct the formation of specific disulfide bonds in the mature peptide region.

The N-terminal peptide generally has the formula:

$$[hAA]_c[pAA]_b[cAA]_a \qquad \text{(Formula 1)}$$

wherein [cAA] is a cleavage site made up of one or more amino acids from which the adjoining mature cysteine-rich peptide can be cleaved by enzymatic action, a is an integer of from about 1 to 10 with integers of about 1 to 5 being preferred; $[pAA]_b$ represents a propeptide domain where b is an integer of between about 5 to 50 with integers of between about 20 to 30 being preferred where pAA represents suitable amino acids forming a peptide chain for proper template homology; $[hAA]_c$ represents a hydrophobic signal sequence where c is an integer of between about 0 and 25 with integers of between about 15 and 25 being preferred wherein the excised region serves as a folding template to direct the formation of said specific disulfide bonds in said cysteine-rich peptide. The amino acids in the N-terminal peptide will generally form a peptide chain [a+b+c] having between about 10 and 85 amino acid residues with a range of between about 15 and 75 being preferred. It has been found that the excised region of the prepropeptides have very significant sequence homology when coupled to mature peptides with similar arrangement of Cysteine residues. These homologies in excised regions appear to extend across species lines, at least in the genus Conus, indicating that it is the excised regions of the molecule which direct folding of specific disulfide bonds in mature peptides. Therefore, it has been found possible to direct formation of specific disulfide bonds in small peptides by coupling the small mature peptide with the appropriate folding template region.

Once the excised region peptide sequence is known, the portions of the prepropeptides that contain the folding instructions can be synthesized and attached to either natural or synthetic small peptides that contain multiple cysteine residues to yield only peptides having the desired specific disulfide bonds. This synthesis can be performed by cloning techniques or by conventional means such as solution phase synthesis, solid phase synthesis or a combination of these techniques. The final prepropeptide resulting from this combination has the disulfide bonds in the proper position for bioactivity. The prepropeptide portion can be enzymatically cleaved from the excised region at site of the basic amino acid moieties as above described without disturbing the disulfide bonds thereby releasing the active cysteine-rich peptide.

DETAILED DESCRIPTION OF THE INVENTION

For most polypeptides to assume a fixed conformation, a minimum size is necessary. Smaller peptides much below fifty amino acids in size are generally considered too small to assume a fixed conformation. In these small peptides the number of hydrogen bonds and other weak attractions between the amino acids of the chain is insufficient to form a rigid or a specific configuration. Therefore, a large number of different conformations can occur in these small peptides. Nature has solved this problem in certain cases by dispersing cysteine residues to form disulfide bonds thereby greatly constraining the small peptide chain. In the Conus venoms an unprecedented diversity of small (10–30 amino acids) disulfide-rich peptides is found. Since most of the small peptides in the Conus system have six cysteine residues, fifteen disulfide bonded configurations are theoretically possible However, in vivo, a single specific disulfide bonded configuration is generated for each peptide Cloning data from several different Conus species has revealed the existence of prepropeptide precursors to the conotoxins. Table 1 contains the amino acid sequence of 5 biologically active "mature" conotoxin molecules. These sequences have been determined by direct peptide sequencing of purified venom duct components. Also shown are amino acid sequences of prepropeptide precursors of each of these toxins as determined by cDNA sequencing of messages expressed in venom duct tissue. Each of these prepromolecules conforms to a general architectural theme. They contain an N terminal hydrophobic signal sequence domain of approximately 20 amino acids followed by a domain of variable length (25–30 amino acids) which is neither signal sequence nor the final biologically active toxin. These two N-terminal domains are excised from the precursor molecule during processing. The third region, at the C-terminal end contains toxin specific sequences and is referred to as the "mature peptide". In each case, one or more basic amino acid residues separate the second and third domains of the prepropeptide, affording a cleavage site for excision of the "mature peptide". Therefore, the present cloning data indicate that most if not all conotoxins are derived from precursor peptides which are each in the size range of molecules such as BPTI (bovine pancreatic trypsin inhibitor)

which are capable of spontaneous precise folding into a specific conformation.

Cloning of several "families" of conotoxins has revealed striking relationships among these prepropeptide precursor molecules. It has been observed that mature conotoxins which have very different amino acid sequences but share a common organization (framework) of cysteine residues are derived from precursor molecules which share significant sequence homology at their N-terminal domains. This data indicates that the two N-terminal domains which are excised during processing (hereinafter called the "template" region) are necessary for the formation of specific disulfide bonds in the mature peptide. The basis for this invention lies in the fact that the same template region can be used to specifically fold mature peptides of considerable sequence diversity, i.e., although the arrangement of cysteine residues is conserved, a wide variety of non-cysteine residue sequences are acceptable. This discovery provides applications for folding small disulfide-rich peptides in vitro and in vivo.

The amino acid sequence of conotoxin precursor molecules has been determined by sequencing cDNA clones which encode these molecules. For these studies, two different types of plasmid based cDNA libraries have been employed. Data for the King Kong family of conotoxins (KK0, KK1, and KK2) has been derived from clones screened from a vector-primed library of *Conus textile* cDNA inserts. This library was constructed using polyA selected mRNA transcripts purified from *Conus textile* venom duct tissue and cloned into the Okyama-Berg oligo-dT primed plasmid pSV7186. cDNA clones were selected using standard colony hybridization procedures and oligonucleotide probes encoding the prepropeptide region of KK0 mRNA. Oligonucleotide probes for this experiment were synthesized based on partial sequencing of KK0 transcript directly from *Conus textile* polyA selected venom duct mRNA using reverse transcriptase. Data for the MVIIb, GVIA, Circler, and GI peptides were derived from clones screened from vector-primed cDNA libraries of *Conus magus* and *Conus geographus* venom duct transcripts. These libraries were created using oligo-dT primed pUC13 vector. cDNA clones were identified using mixed oligonucleotide probes encoding all permutations of the universal codon sequence for 6 amino acid portions of each mature toxin. Colonies were plated onto nitrocellulose filters and grown on nutrient broth plates containing 50 μ/ml kanamycin sulfate and 50 μg/ml ampicillin. Replica filters were transferred to Whatman filter paper wet with lysis buffer containing 0.5M NaOH and 1.5M NaCl. Following serial neutralization in 0.5M tris pH 8.0, 1.5M tris pH 8.0 and 1.5M NaCl, filters were dried at 80° C. in a vacuum oven. Filters were pre-washed in a solution containing 3M tetramethylammonium chloride (TMAC), 50 mM tris and 0.2% SDS. Filters were pre-hydribized at 48° C. for 4 hours and hybridized for 40-60 hours in a solution containing 3M TMAC, 0.1M NaPhosphate, 1 mM EDTA, 5×Denhardt's solution, 0.6% SDS and 100 μg/ml salmon sperm DNA. In addition, the hybridization solution contained mixed oligonucleotide probes end-labelled using $\tau P^{32}$ ATP and T4 DNA kinase. Following hybridization, filters were washed at room temperature in a solution containing 3M TMAC,50mM tris pH 8.0 and 0.2% SDS. Final washing was done at 50° C. in a solution containing 2XSSC and 0.1% SDS. Following drying and autoradiography on photographic film, putative conotoxin cDNA clones were picked from replica filters kept on agar plates. In all cases, nucleic acid sequence was determined by direct double strand sequencing of cDNA clones using standard procedures.

EXAMPLE 1

Calcium Channel 4 loop Toxins

Several different conotoxins which target presynaptic calcium channels have previously been characterized. These toxins have largely overlapping specificities for different calcium targets in neuronal tissue preparations. Structurally, these toxins are found to conform to a conserved number and arrangement (framework) of cysteine residues. Each member of this class forms a 4 loop folded toxin molecule with a specific arrangement of cysteines referred to as the omega (ω) pattern. cDNA clones for several members of the ω-conotoxin family were obtained and their nucleic acid sequence determined by the general cloning and sequencing methods above.

Sequences for two members of this family, MVIIB from *Conus magus* and GVIA from *Conus geographus* are illustrated in Table 1. MVIIB and GVIA are 4 loop ω-toxins which contain 25 and 27 amino acids respectively. Their cysteine frameworks vary only in the exact amino acid spacing of the two carboxy terminal intercys domains. Beyond the similarity of framework, the two mature toxins are remarkably divergent. Only nine of the 21 non-cysteine amino acids of the ω-GVIA are conserved in ω-MVIIA. sequence for each of these toxins. MVIIB and GVIA template domains are each 45 amino acids in length. In addition, they show a >90% conservation of amino acid sequence with only 4 positions of amino acid non-identity. These two sequences therefore illustrate the existence of two highly conserved template domains associated with two structurally dissimilar toxins. These features are illustrated in the following sequence representation wherein the respective domains or regions are identified as in Formula 1 where "←→" represents an interface or melding of the regions:

```
(MVIIB) (SEQ. ID NO: 19)
MKLTCVVIVAVLLLTACQLI TADDS RGTQKHRALRS DTKLS MS—TR

¦←————————[hAA]—————————    ————[pAA]——  —  —  ——  →¦cAA¦

MKLTCVVIVAVLLLTACQLI TADDS RGTQKHRALGS TTELSLS—TR
(GVIA) (SEQ. ID NO: 20)
```

TABLE 1

| # | Type/ Name | Mature Toxin determined by amino acid sequencing** | Prepropeptide determined from cDNA clones* |
|---|---|---|---|
| I | 4 loop | | |
| a. | M-7B | [seq. ID NO: 2] CKGKGASCHRTSYDCCTGSCNRGKC | [seq. ID NO: 1] MKLTCVVIVAVLLLTACQLITADDSRGTQ KHRALRSDTKLSMSTRCKGKGASCHRTSY DCCTGSCNRGDCG |
| b. | G-6A | [seq. ID NO: 4] CKSPGSSCSPTSYNCCRSCNPYTKRCY | [seq. ID NO: 3] MKLTCVVIVAVLLLTACQLITADDSRGTQ KHRALGSTTELSLSTRCKSPGSSCSPTSY NCCRSCNPYTKRCYG |
| II | 4 loop | | |
| a. | KK0 | [seq. ID NO: 6] WCKQSGEMCNLLDQNCCDGYCIVLVCT | [seq. ID NO: 5] MKLTCMMIVAVLFLTAWTFATADDPRNGL GNSFSNAHHEMKNPEASKLNKRWCKQSGE MCNLLDQNCCDGYCIVLVCT |
| b. | KK1 | [seq. ID NO: 8] CIEQFDPCEMIRHTCCVGVLFLMACI | [seq. ID NO: 7] MKLTCMMIVAVLFLTAWTFATADDSGNGL ENSFSKAHHEMKNPEASKLNKRCIEQFDP CEMIRHTCCVGVCFLMACI |
| c. | KK2 | [seq. ID NO: 10] CAPFLHPCTFFFPTCCNSYCVQFICL | [seq. ID NO: 9] MKLTCMMIVAVLFLTAWTFVTADDSGNGL ENSFSKAHHEMKNPEASNLNKRCAPFLHP CTFFFPTCCNSYCVQFICL |
| III | 3 loop | | |
| | CIRC | [seq. ID NO: 12] CCPPVACNMGCKPCC | [seq. ID NO: 11] MSKLGALLTICLLLFSLTAVPLDGDQHAD QPAQRLQDRIPTEDHPLFDPNKRCCPPVA CNMGCKPCCG |
| IV | 2 loop | | |
| | GI | [seq. ID NO: 14] ECCNPACGRHYSC | [seq. ID NO: 13] MGMRMMFTVFLLVVLATTVVSFFSERASD GRDDTAKDEGSDMDKLVEKKECCNPACGR HYSCGR |

*Sequences with G or GR at the C-terminus are post-translationally processed to give a C-terminal amide in the mature toxin or peptide.
**P in a sequence stands for hydroxyproline.

Example 2

Another family of conotoxin prepropeptides has been derived from sequencing of cDNA done from the mollusk hunting species *Conus textile*. The king Kong peptide is a 27 amino acid toxin which is phenotypically inactive when injected either intraperitoneally or intracerebrally in mice. However, it has been shown to elicit dominant posturing when injected into lobsters and to cause a rhythmic undulation in mollusks.

The primary sequence of the King Kong peptide [Seq. ID No: 6] (shown below) was determined by amino acid sequencing as described by Hillyard et al., *Biochemistry*, 28, 358-361(1988).

W—C—K—Q—S—G—
E—M—C—N—L—L—D—Q—N—C—C—D—
G—Y—C—I—V—L—V—C—T

The horizontal bars show the amino acids encoded by the 14 and 20 nucleotide mixed probes that were used as primers in the RNA sequencing reaction. The probe to the more N-terminal region was a mixture of 16 different oligonucleotides, and the more C-terminal probe had a degeneracy of 64. The mixed oligonucleotides were then used for sequencing poly(a)+RNA from *Conus textile* venom ducts. The sequence obtained was used for probing a *Conus textile* venom duct cDNA library. Detailed methods follow:

SYNTHESIS OF OLIGONUCLEOTIDES

Mixed oligonucleotides corresponding to two regions of the King-Kong peptide were synthesized using an Applied Biosystems 380B synthesizer, a 20 base oligonucleotide 5′ CCRTCRCARCARTTYTGRTC 3′ [Seq. ID No: 15] and a 14 base oligonucleotide 5′ TTRCACATYTCNCC 3′ [Seq. ID No: 16](R=A or G, Y=T or C and N=ATG or C). These correspond to the amino acid sequences DQNCCDG [Seq. ID No: 17] and GEMCN [Seq. ID No: 18] of the King-Kong peptide.

SEQUENCING OF RNA

RNA was isolated from ~20 C.textile venom ducts that had been previously dissected and frozen at −80° C. The tissue was pulverized using a mortar ad pestle in liquid nitrogen and lysed in the presence of guanidinium thiocyanate according to published procedures (Chirgwin et al., *Biochemistry*, 18, 5294-5299,(1979)). Poly(A)+ RNA was prepared by two passes of the total RNA over an oligo(dT) column (Maniatis et al., *Molecular Cloning: Laboratory Manual*, Cold Spring Harbor Laboratory Press, Cold Spring Harbor, NY, (1982)).

Approximately 1 μg of poly(A) RNA in distilled $H_2O$ was denatured by heating to 95° C. for 10 min, then quenched on ice for 5 min. Sixteen picomols of either of the two oligomers above that had been labeled using T4

DNA kinase and [$\gamma$-$^{32}$P] ATP were added and annealed in the presence of 5 mM Tris-HCl, pH 8.3, 6 mM NaCl, 1 mM DTT at 37° C. for 10 min. $Mg(OAc)_2$ was added to 6 mM and the mixture divided into four tubes corresponding to the following mixes of nucleotides: 0.36 mM each of dATP, dGTP, dCTPPP and dTTP, 0.2 mM of either ddATP, ddCTP, ddGTP or ddTTP and 0.5 U of reverse transcriptase (Seikagaku) in a total volume of 5.0 ml, incubated for a total of 30 min at 52° C. The reactions were stopped with 10 ml of loading dye consisting of 0.04% xylene cyanol, 0.04% bromophenol blue, 1×TBE buffer (0.089M Tris-borate, 0.089M boric acid, 2 mM EDTA) and formamide, and heated to 95° C. for 2 min before loading on a 7.5% acrylamide/7M urea sequencing gel. The sequence obtained spanned 178 nucleotides including five N-terminal amino acids of the King-Kong peptides.

A total of 20 000 colonies were plated out and duplicate membrane filter lifts prepared One set of filters was hybridized to probes A and B and the other set to probes C or D using the same conditions as above. The filters using intensifying screens at −80° C. for 24 h. Colonies that were positive for both oligomer probes A and B or probes C. and D were picked, single colonies isolated and 5 ml mini-plasmid preparations prepared.

Putative plasmid clones were sequenced using a double stranded sequencing protocol with Sequenase (Kraft et al., *Biotechniques,* 6, 544–546, (1988)) and sequencing primers corresponding to both ends of the vector pSV7186 (Okayama, H. and Berg, P. Mol. Cell. Biol., 2, 161–170 (1982)).

The sequences obtained encoded the prepropeptide sequences shown in Table I and FIGS. 2A and 2B below.

FIG. 2 A

```
KK0...MKLTCMNIVAVLFLTAWTFATADDPRNGLGNFLSNAHHEMKNPEASKLNKRWCKQSGEMCNL LDQNCCDGYCI VLVCT
KK1                          SS    E    K                     . I EQFDP  EMI RHT  V  V FLMA I
KK2                     V    SG    E    K             N       . APFLHP  TF FFP    NS V VQF I  L
```

FIG. 2 B

| | | | | | | | | | |
|---|---|---|---|---|---|---|---|---|---|
| KK-0 | W C | K Q S S E M | C | N L L D Q N | C C | D G Y | C | I V L V | C T |
| KK-1 | C | I E Q F D P | C | E M I R H T | C C | V G V | C | F L M A | C I |
| KK-2 | C | A P F L H P | C | T F F F P N | C C | N S Y | C | V Q F I | C L |

cDNA LIBRARY CONSTRUCTION

A library was constructed in the Okayama-Berg vector pSV7186 (Okayama and Berg, 1982) using ~1.5 mg of oligo(dT) selected poly(A) +RNA from venom duct isolated as above. Approximately 3.2 ×10 independent colonies were obtained after transformation into *Escherichia coli* DH5 competent cells. DNA from 24 clones was prepared from minipreps of 5 ml overnight cultures. Upon restriction digestion and analysis, 92% of these clones appeared to have inserts ranging in size from 150 to 2700 bases. The library was amplified and stored in 15% DMSO AT −80° C.

SCREENING OF cDNA LIBRARIES

To identify individual clones containing the King-Kong peptide sequence, two 16 base oligonucleotides were synthesized. Probe C corresponds to the mRNA sequence, as determined above, of the five most N-terminal acids, WCKSQ, and probe D corresponds to the complementary sequence. Approximately 16 pmol of probes C and D Were kinased and hybridized to duplicate blots for 10 h at 42° C. in 6×NET, 5×Denhardt's, 0.1% SDS and 100 mg/ml sonicated salmon testis DNA. Blots were washed to a final stringency of 2 SSC, 0.1% SDS at 42° C. To identify clones containing the 5' flanking sequences two overlapping 90 base oligonucleotides (probes A and B), corresponding to the region 5' of the King-Kong peptide, who sequence was determined by the RNA sequencing, were synthesized as above. Approximately 16 pmol each of probes A and B were kinased and hybridized to duplicate blots at 52° C. in 6×NET, 5×Denhardt's, 0.1% SDS and 100 mg/ml sonicated salmon testes DNA. Blots were washed at a final stringency of 0.1×SSC, 0.1% SDS at 65° C. for 15 min.

The above tables show the propeptides encoded by the KK0, KK1 and KK2 sequences. It is notable that in the 51 amino acid excised N-terminal flanking region there is only one position which is different In all three sequences [Seq. ID No: 21, Seq. ID No: 22, and Seq. ID No: 23]; in contrast, except for cysteine residues, no residues are entirely conserved and 16 out of 20 positions have different residues in all three sequences in the peptide toxin region. The putative final processed peptides predicted form potential protease cleavage sites and stop signals are shown in Part B.

OTHER EXAMPLES

The cDNA sequencing of toxins representative of two other cysteine framework types have been determined. The circler toxin is found in the venom of *Conus textile* and has a 3 loop cysteine framework as shown in Row III in Table I. This framework is also seen in toxins which target skeletal muscle Na+ channels. When the sequence of the circler toxin "excised region" [Seq. ID No: 24] is compared to any of the 4 loop prepropeptides cited above, no significant sequence homology is noted. This is true even for toxins from the King Kong family which are derived from the same species as the circler toxin. Sequence comparisons for the acetylcholine receptor targeting toxin GI from *Conus geographus* have also been made. This toxin has 4 cysteine residues and forms a two loop cysteine framework as shown in Row IV of Table I. The "excised region" [Seq. ID No: 25] of the GI prepropeptide shows no significant sequence homology to any of the 3 or 4 loop conotoxin precursors.

In summary, it can be seen that the methods and compositions of the above invention provide an advancement in the art of synthesizing small disulfide-rich peptides. In particular, the invention demonstrates that a segregated template sequence directs specific disulfide bond formation in mature peptides that have considerable diversity in amino acid sequence. The segregation of template and mature peptide sequences, and the ability of essentially conserved templates to direct specific disulfide bonding in diverse peptides, gives the invention more general applicability to synthesizing disulfide-rich peptides, particularly by cloning methods. Specific disulfide bonding can be directed even under conditions where sequences in the mature peptide are being varied.

While certain representative embodiments of the invention have been described herein for purposes of illustration, the invention may be embodied in other specific forms without departing from its spirit or essential characteristics, and the described examples should not be considered restrictive, but only illustrative. The scope of the invention is therefore defined by the appended claims rather than by the foregoing examples.

What is claimed is:

1. A method of forming a mature biologically active cysteine-rich peptide having specific disulfide bonds between cysteine residues providing a consistent folding pattern which comprises the formation, by cloning methods, solution phase synthesis or solid phase synthesis, or a combination of solution phase synthesis and solid phase synthesis, of a prepropeptide consisting of a C-terminal excised region separated from said cysteine-rich peptide by one or more cleavable amino acid residues wherein the sequence of the N-terminal excised region is derived from conotoxin peptides found in Conus venom and serves as a folding template to direct the formation of said specific disulfide bonds in said cysteine-rich peptide, and then cleaving said mature peptide form said prepropeptide.

2. The method according to claim 1 wherein the N-terminal excised region and cleavable amino acid residues are represented by the formula:

$$[hAA]_c[pAA]_b[cAA]_a$$

wherein $[cAA]_a$ is a cleavage site made up of one or more amino acids from which the adjoining mature cysteine-rich peptide is cleaved by enzymatic action, a is an integer of from about 1 to 10; $[pAA]_b$ represents a propeptide domain where b is an integer of between about 5 to 50 where pAA represents suitable amino acids forming a peptide chain of proper template homology; $[hAA]_c$ represents a hydrophobic signal sequence where c is an integer of between about 0 and 25 wherein the N-terminal region peptide chain represented by the sum of integers a,b and c will contain between about 10 and 85 amino acid residues.

3. The method of claim 2 wherein a is an integer of between about 1 and 5.

4. The method of claim 2 wherein b is an integer of between about 20 to 30.

5. The method of claim 2 wherein c is an integer of between about 15 and 25.

6. The method of claim 2 wherein a is an integer of between about 1 and 5, b is an integer of between about 20 to 30, c is an integer of between about 15 and 25 and the sum of a, b and c is an integer of between about 15 and 75.

7. The method of claim 1 wherein the prepropeptide N-terminal template region is derived from *Conus magus* venom.

8. The method of claim 1 wherein the prepropeptide N-terminal template region is derived from *Conus geographus* venom.

9. The method of claim 1 wherein the prepropeptide N-terminal template region is derived from *Conus textile* venom.

10. The method of claim 6 wherein the prepropeptide is formed by cloning methods.

11. The method of claim 6 wherein the prepropeptide is formed by solid phase synthesis methods.

12. The method of claim 6 wherein the prepropeptide is formed by solution phase synthesis methods.

13. The method of claim 6 wherein the prepropeptide is formed by a combination of solid phase synthesis and solution phase synthesis.

* * * * *